US 6,413,245 B1

(12) United States Patent
Yaacobi et al.

(10) Patent No.: US 6,413,245 B1
(45) Date of Patent: Jul. 2, 2002

(54) SUB-TENON DRUG DELIVERY

(75) Inventors: Yoseph Yaacobi, Fort Worth; Abbot F. Clark, Arlington; David C. Dahlin, Arlington; Craig B. Struble, Arlington; David Allen Marsh, Fort Worth; Billie M. York, Conroe, all of TX (US)

(73) Assignee: Alcon Universal Ltd., Hunenberg (CH)

( * ) Notice: Subject to any disclaimer, the term of this patent is extended or adjusted under 35 U.S.C. 154(b) by 126 days.

(21) Appl. No.: 09/677,656

(22) Filed: Oct. 4, 2000

Related U.S. Application Data

(60) Provisional application No. 60/161,660, filed on Oct. 21, 1999.

(51) Int. Cl.$^7$ .......................... A61M 25/00; A61M 31/00

(52) U.S. Cl. ........................ 604/264; 604/48; 604/521

(58) Field of Search ............................ 604/264, 272, 604/48, 506, 521

(56) References Cited

U.S. PATENT DOCUMENTS

| 3,416,530 A | 12/1968 | Ness ........................... 128/260 |
| 3,439,675 A | 4/1969 | Cohen .......................... 128/239 |
| 3,828,777 A | 8/1974 | Ness ........................... 128/260 |
| 4,014,335 A | 3/1977 | Arnold ......................... 128/260 |
| 4,300,557 A | 11/1981 | Refojo et al. ................. 128/260 |

(List continued on next page.)

FOREIGN PATENT DOCUMENTS

| EP | 0 904 787 | 3/1999 | .......... A61K/47/30 |
| WO | WO 93/20784 | 10/1993 | ............. A61F/9/00 |
| WO | WO 94/05257 | 3/1994 | ............. A61K/9/00 |
| WO | WO 95/26734 | 10/1995 | .......... A61K/31/70 |
| WO | WO 95/28984 | 11/1995 | .......... A61M/25/00 |

(List continued on next page.)

OTHER PUBLICATIONS

"Bausch & Lomb and Control Delivery Systems Agree to Develop Breakthrough Therapeutic Products for Severe Eye Diseases"; Business Wire via First!; NewsEdge Corp.; Jun. 14, 1999; 4 pp.

"Method of Placing Irrigation System into Tenon's Space", E.I. Sidorenko, et al., Abstract of Russian Patent No. RU 2123314, issued Dec. 20, 1998, 1 pg.

"A New Method for Posterior Sub–Tenon's Drug Administration", Nesterov et al., Ophthalmic Surgery, vol. 24, No. 1, Jan. 1993, pp. 59–61.

*Uveitis: A Clinical Approach to Diagnosis and Management (Second Edition)*; Smith et al.; 1989, pp. 51–76.

"Sub–Tenon's anaesthesia: an efficient and safe technique", Roman et al., *British Journal of Ophthalmology*, 81:8, 1997, pp. 673–676.

"Single Quadrant Sub–Tenon's Block: Evaluation of a New Local Anaesthetic Technique for Eye Surgery", Anaesthesia and *Intensive Care* 24: 241–244, Apr. 1996.

(List continued on next page.)

*Primary Examiner*—Gregory Huson
*Assistant Examiner*—Kathleen J. Prunner
(74) *Attorney, Agent, or Firm*—W. David Lee

(57) ABSTRACT

Disclosed is a method and apparatus for delivering a drug formulation to a human eye. The method includes the steps of inserting the apparatus below the Tenon's capsule and above the sclera at a point posterior to the limbus of the eye and injecting the drug formulation to form a drug depot on an outer surface of the sclera. The apparatus includes a cannula having a distal portion, a proximal portion, and a bend separating the distal portion and the proximal portion. The distal portion has a radius of curvature substantially equal to a radius of curvature of the globe of the eye. A tangent of the distal portion at the bend is disposed at an angle no more than about 56 degrees with respect to the proximal portion.

36 Claims, 5 Drawing Sheets

U.S. PATENT DOCUMENTS

| | | | |
|---|---|---|---|
| 4,327,725 A | 5/1982 | Cortese et al. | 128/260 |
| 4,759,756 A | 7/1988 | Straus | 604/51 |
| 4,853,224 A | 8/1989 | Wong | 242/427 |
| 4,946,450 A | 8/1990 | Erwin | 604/294 |
| 4,997,652 A | 3/1991 | Wong | 424/428 |
| 5,127,831 A | 7/1992 | Bab | 433/80 |
| 5,147,647 A | 9/1992 | Darougar | 424/427 |
| 5,164,188 A | 11/1992 | Wong | 424/428 |
| 5,167,618 A | 12/1992 | Kershner | 604/22 |
| 5,178,635 A | 1/1993 | Gwon et al. | 623/4 |
| 5,300,114 A | 4/1994 | Gwon et al. | 623/4 |
| 5,322,691 A | 6/1994 | Darougar et al. | 424/427 |
| 5,378,475 A | 1/1995 | Smith et al. | 424/473 |
| 5,403,901 A | 4/1995 | Namdaran et al. | 526/259 |
| 5,443,505 A | 8/1995 | Wong et al. | 623/4 |
| 5,466,466 A | 11/1995 | Muller | 424/449 |
| 5,476,511 A | 12/1995 | Gwon et al. | 623/4 |
| 5,516,522 A | 5/1996 | Peyman et al. | 424/426 |
| 5,632,984 A | 5/1997 | Wong et al. | 424/85.4 |
| 5,665,069 A | 9/1997 | Cumer et al. | 604/116 |
| 5,679,666 A | 10/1997 | Clark | 514/179 |
| 5,725,493 A | 3/1998 | Avery et al. | 604/9 |
| 5,743,274 A | 4/1998 | Peyman | 128/898 |
| 5,766,242 A | 6/1998 | Wong et al. | 623/4 |
| 5,766,619 A | 6/1998 | Aiache et al. | 424/427 |
| 5,770,592 A | 6/1998 | Clark | 514/179 |
| 5,773,019 A | 6/1998 | Ashton et al. | 424/423 |
| 5,797,898 A | 8/1998 | Santini, Jr. et al. | 604/890 |
| 5,817,075 A | 10/1998 | Giungo | 604/294 |
| 5,824,072 A | 10/1998 | Wong | 623/4 |
| 5,824,073 A | 10/1998 | Peyman | 623/4 |
| 5,830,173 A | 11/1998 | Avery et al. | 604/9 |
| 5,836,935 A | 11/1998 | Ashton et al. | 604/891.1 |
| 5,902,598 A | 5/1999 | Chen et al. | 424/423 |
| 5,904,144 A | 5/1999 | Hammang et al. | 18/898 |
| 5,916,584 A | 6/1999 | O'Donoghue et al. | 424/426 |
| 6,001,386 A | 12/1999 | Ashton et al. | 424/423 |
| 6,028,099 A | 2/2000 | de Juan, Jr. | 514/434 |
| 6,074,661 A | 6/2000 | Olenik et al. | 424/427 |
| 6,126,687 A | 10/2000 | Peyman | 623/4 |
| 6,135,984 A | 10/2000 | Dishler | 604/264 |

FOREIGN PATENT DOCUMENTS

| | | | |
|---|---|---|---|
| WO | WO 96/36377 | 11/1996 | A61M/5/00 |
| WO | WO 99/07418 | 2/1999 | A61L/27/00 |
| WO | WO 99/11244 | 3/1999 | A61K/9/22 |
| WO | WO 99/45920 | 9/1999 | A61K/31/35 |
| WO | WO 00/07530 | 2/2000 | A61F/9/00 |
| WO | WO 00/07565 | 2/2000 | A61K/9/00 |

OTHER PUBLICATIONS

"Curved, Sub–Tenon Cannula for Local Anaesthesia", Julian Stevens, *Ophthalmic Surgery*, 24: 121–122, Feb. 1993.

"A Modified Sub–Tenon's Cannula for Local Anesthesia", Muthusamy et al., Asia–Pacific Journal of Ophthalmology, vol. 8, No. 3, Jul. 1996; 6 pp.

Katena Eye Instruments, Catalog Supplement, Katena Products, Inc., 1997, 3 pp.

"Ocular Anesthesia for Cataract Surgery: A Direct Sub–Tenon's Approach", Hansen et al., *Ophthalmic Surgery*, vol. 21, No. 10, 1990, pp. 696–699.

"Local Anesthesia for Vitreoretinal Surgery", Mein et al., *Retina*, 10:47–49, 1990.

"Echographic Localization of Corticosteriods After Periocular Injection", Freeman et al., *American Journal of Ophthalmology*, 103:281–288, Mar. 1987.

"Prospective Study of Sub–Tenon's versus Retrobulbar Anesthesia for Inpatient and Day–surgery Trabeculectomy", Buys et al., *Ophthalmology*, vol. 100, No. 10, Oct. 1993, pp. 1585–1589.

Internet printouts for Eagle Laboratories Tri–Port Sub–Tenon (Mendez) 100–19, 100–19C, 100–21, 100–21C cannulas, 1 page.

Internet printouts for Moria, Inc. 111275G (25G Retrobulbar Curved (Uthoff), 121278 (19G Sub–Tenon) cannulas, 1 page.

SUB-TENON DRUG DELIVERY

This application claims the benefit of U.S. Provisional Application Serial No. 60/161,660, filed Oct. 21, 1999, which is incorporated herein in its entirety by this reference.

FIELD OF THE INVENTION

The present invention generally pertains to the delivery of ophthalmically acceptable pharmaceutically active agents to the back of the eye. More particularly, but not by way of limitation, the present invention pertains to apparatus and methods for sub-Tenon delivery of a drug depot to the posterior segment of a human eye proximate the macula.

DESCRIPTION OF THE RELATED ART

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, and glaucoma are several examples.

Age related macular degeneration (ARMD) is the leading cause of blindness in the elderly. ARMD attacks the center of vision and blurs it, making reading, driving, and other detailed tasks difficult or impossible. About 200,000 new cases of ARMD occur each year in the United States alone. Current estimates reveal that approximately forty percent of the population over age 75, and approximately twenty percent of the population over age 60, suffer from some degree of macular degeneration. "Wet" ARMD is the type of ARMD that most often causes blindness. In wet ARMD, newly formed choroidal blood vessels (choroidal neovascularization (CNV)) leak fluid and cause progressive damage to the retina.

In the particular case of CNV in ARMD, two main methods of treatment are currently being developed, (a) photocoagulation and (b) the use of angiogenesis inhibitors. However, photocoagulation can be harmful to the retina and is impractical when the CNV is in proximity of the fovea. Furthermore, photocoagulation often results in recurrent CNV over time. Oral administration of anti-angiogenic compounds is also being tested as a systemic treatment for ARMD. However, due to drug-specific metabolic restrictions, systemic administration usually provides sub-therapeutic drug levels to the eye. Therefore, to achieve effective intraocular drug concentrations, either an unacceptably high dose or repetitive conventional doses are required. Various implants have also been developed for delivery of anti-angiogenic compounds locally to the eye. Examples of such implants are disclosed in U.S. Pat. Nos. 5,824,072 to Wong, U.S. Pat. No. 5,476,511 to Gwon et al., and U.S. Pat. No. 5,773,019 to Ashton et al.

In addition, it is known to use a straight, ⅝ inch long, 25 gauge needle to perform sub-Tenon injection of corticosteroids for the treatment of posterior uveitis or macular edema associated with uveitis or anterior segment surgery. See *Uveitis: A Clinical Approach to Diagnosis and Management (Second Edition)*, Ronald E. Smith and Robert A. Nozik, 1989, pp. 63–68; "Echographic Localization of Corticosteroids After Periocular Injection", William R. Freeman, Ronald L. Green, and Ronald E. Smith, *American Journal of Ophthalmology* 103:281–288, March 1987. In such methods, a physician attempts to dispose the tip of the needle near the macula but without penetrating the posterior ciliary arteries or the optic nerve. However, because the physician cannot see the tip, as well as movement of the eyeball within the orbit due to contact with the straight needle, it is very difficult to precisely place the tip at the desired location near the macula. For the same reasons, it is also very difficult to determine whether the tip is correctly positioned below the Tenon's capsule. Such methods do not insure a consistent delivery of a specific quantity of drug to a region over the macula. In fact, the literature reports that only about 57 percent of injections using this method result in drug being placed in the sub-Tenon space overlying the macular area. "Echographic Localization of Corticosteroids After Periocular Injection", pp. 283–285. In addition, moving a straight needle along the curved surface of the sclera causes "tenting" or stretching of the overlying Tenon's capsule. Such movement may cause penetration of the Tenon's capsule, allowing drug to be injected into surrounding tissues. Furthermore, such movement may also cause inadvertent penetration of the sclera, resulting in injection of drug into the vitreous cavity. More importantly, penetration of the sclera may result in significant damage to the eye or even a loss of sight. Documented complications of such penetrations include orbital hemorrhage, central retinal vein occlusion, and central retinal artery occlusion.

Referring to FIG. 6, it is also known to use a blunt 19 gage cannula 200 having a hub 201, a straight proximal portion 202, and an angled distal portion 204 to perform sub-Tenon injection of anesthesia for cataract and vitreoretinal surgery. See "Local Anesthesia for Vitreoretinal Surgery", Calvin E. Mein and Michael G. Woodcock, *Retina* 10: 47–49, 1990; "Ocular Anesthesia for Cataract Surgery: A Direct Sub-Tenon's Approach", *Ophthalmic Surgery* 21:696–699, 1990; "Single Quadrant Sub-Tenon's Bock: Evaluation of a New Local Anaesthetic Technique for Eye Surgery", *Anaesthesia and Intensive Care* 24: 241–244, April 1996. However, such cannulae also suffer from the above-described "tenting" and penetration problems if used to deliver drugs into the sub-Tenon's space above the macula.

It is also known to use a gently curved cannula 210 as shown in FIG. 7 to perform sub-Tenon injection of anesthesia for cataract surgery. See "Curved, SubTenon Cannula for Local Anesthesia", Julian D. Stevens, *Ophthalmic Surgery*, 24:121–122, February 1993. However, this cannula also suffers from the above-described "tenting" and penetration problems if used to deliver drugs into the subTenon's space above the macula.

It is also known to use a 24 gauge cannula that has a straight proximal portion and a curved distal portion that is disposed at a 90 degree angle to the straight portion to inject a local anesthetic solution below the Tenon's capsule. The straight portion has a length of 5 mm. The curved portion has a radius of curvature of 14 mm and an arc length of 27 mm. See "A Modified Sub-Tenon's Cannula for Local Anesthesia", P. Muthusamy and Richard F. Hommersom, *Asia-Pacific Journal of Ophthalmology*, Volume 8, No. 3 (July 1996). However, because of its geometry, this cannula is not suitable for the delivery of drugs in the form of suspensions, emulsions, ointments, or gels, or drugs in such forms including bioerodable polymers or non-bioerodable polymers.

Therefore, a need exists in the field of ophthalmology for improved apparatus and methods for sub-Tenon delivery of a drug depot to the posterior segment of a human eye proximate the macula that do not suffer from the above-described limitations. The improved apparatus and methods should be safe for the patient, easy for the physician to use, capable of delivering a wide spectrum of formulations, and capable of being performed in an outpatient setting.

SUMMARY OF THE INVENTION

One aspect of the present invention comprises a cannula including a distal portion having a radius of curvature substantially equal to a radius of curvature of a globe of the human eye, a proximal portion, and a bend separating the distal portion and the proximal portion. A tangent of the distal portion at the bend is disposed at an angle of no more than about 56 degrees with respect to the proximal portion.

In another aspect, the present invention comprises a method of delivering a drug to the human eye. A cannula is inserted below the Tenon's capsule and above the sclera of the human eye at a point posterior to a limbus of the eye. The cannula includes a distal portion having a radius of curvature substantially equal to a radius of curvature of the globe of the human eye. A drug is injected through the cannula to form a drug depot on an outer surface of the sclera. The drug comprises a pharmaceutically active agent selected from the group consisting of 4,9(11)Pregnadien-17α,21-diol-3,20-dione and 4,9(11)-Pregnadien-17α, 21-diol-3,20-dione-21-acetate.

In another aspect, the present invention comprises a cannula including a hub for removably coupling to a syringe, a proximal portion, and a distal portion. The distal portion has a tip, an orifice proximate the tip, and a radius of curvature substantially equal to a radius of curvature of the globe of the human eye. The part of the distal portion proximate the tip comprises a plastic.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1 through 5 of the drawings, like numerals being used for like and corresponding parts of the various drawings.

Figure 1:
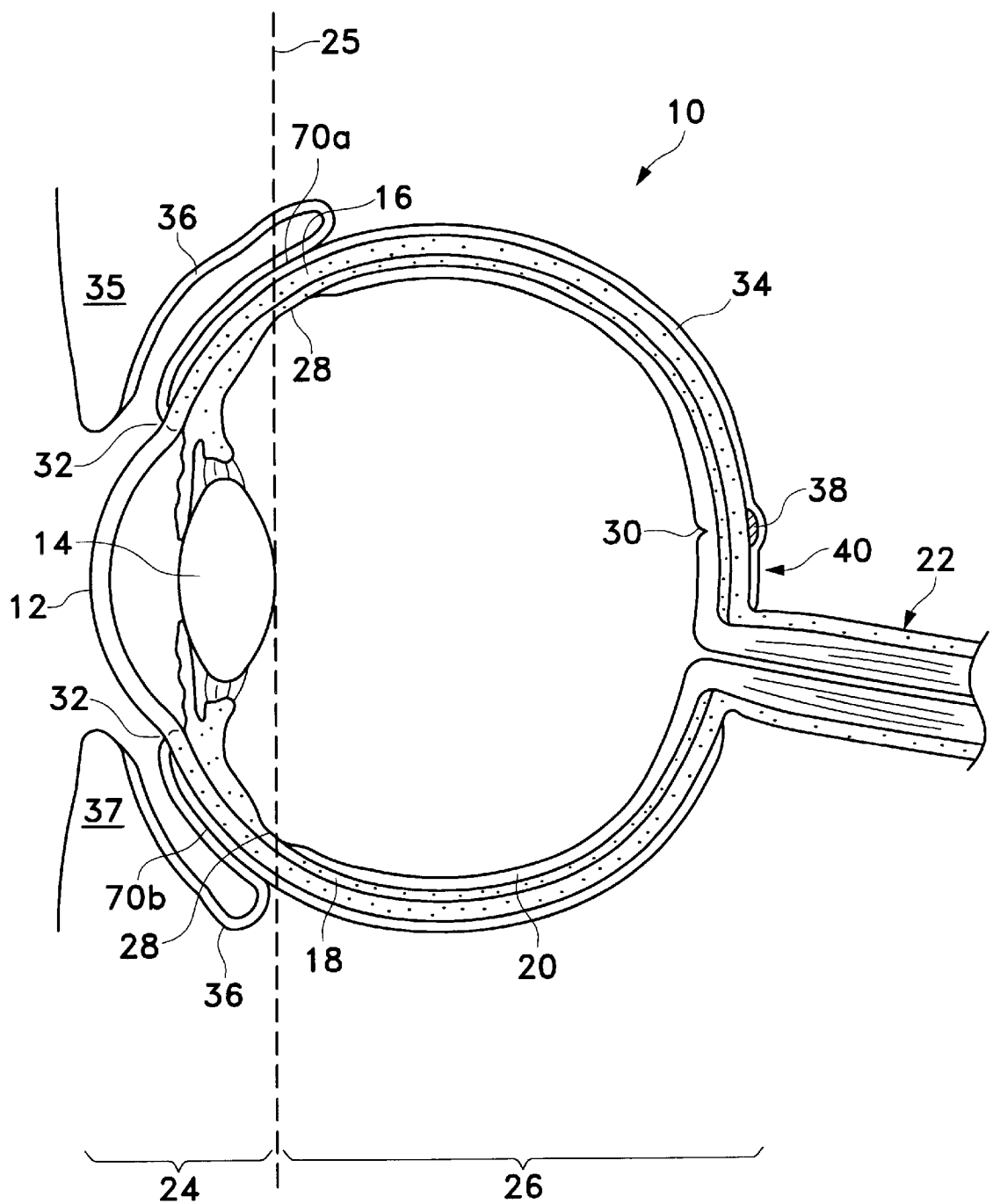
FIG. 1 is a side sectional view schematically illustrating the human eye and a drug depot according to a preferred embodiment of the present invention.

FIG. 1 schematically illustrates a human eye 10. Eye 10 has a cornea 12, a lens 14, a sclera 16, a choroid 18, a retina 20, and an optic nerve 22. An anterior segment 24 of eye 10 generally includes the portions of eye 10 anterior of line 25. A posterior segment 26 of eye 10 generally includes the portions of eye 10 posterior of line 25. Retina 20 is physically attached to choroid 18 in a circumferential manner proximate pars plana 28. Retina 20 has a macula 30 located slightly lateral to optic nerve 22. As is well known in the ophthalmic art, macula 30 is comprised primarily of retinal cones and is the region of maximum visual acuity in retina 20. A Tenon's capsule or Tenon's membrane 34 is disposed on sclera 16. A conjunctiva 36 covers a short area of the globe of eye 10 posterior to limbus 32 (the bulbar conjunctiva) and folds up (the upper cul-de-sac) or down (the lower cul-de-sac) to cover the inner areas of upper eyelid 35 and lower eyelid 37, respectively. Conjunctiva 36 is disposed on top of Tenon's capsule 34.

Sclera 16 and Tenon's capsule 34 define the exterior surface of the globe of eye 10. For treatment of ARMD, CNV, retinopathies, retinitis, uveitis, cystoid macular edema (CME), glaucoma, and other diseases or conditions of posterior segment 26, it is preferable to dispose a depot 38 of a specific quantity of an ophthalmically acceptable pharmaceutically active agent directly on the outer surface of sclera 16 and below Tenon's capsule 34. In addition, in cases of ARMD and CME it is most preferable to dispose depot 38 directly on the outer surface of sclera 16, below Tenon's capsule 34, and generally above macula 30. In a study using New Zealand White rabbits, a drug depot of 4,9(11)-Pregnadien-17α,21-diol-3,20-dione-21-acetate, an angiostatic steroid available from Steraloids, Inc. of Wilton, New Hampshire, was disposed directly on the outer surface of the sclera, below the Tenon's capsule, and slightly posterior of the equator of the rabbit eyes. Such a drug depot resulted in a concentration of the angiostatic steroid, averaged over the entire retina and measured the day after the injection, about ten times greater than a similar concentration delivered by a depot located below the conjunctiva but above the Tenon's capsule of the rabbit eyes. Given the fact that the Tenon's capsule of a New Zealand White rabbit is very thin, these beneficial results are highly unexpected. It is important to note that Tenon's capsule 34 of human eye 10 is also very thin. 4,9(11)Pregnadien-17α,21-diol-3,20-dione-21-acetate, and the related compound 4,9(11)-Pregnadien-17α,21-diol-3,20-dione, are more fully described in U.S. Pat. Nos. 5,770,592 and 5,679,666, which are incorporated herein in their entirety by reference.

Figure 2:
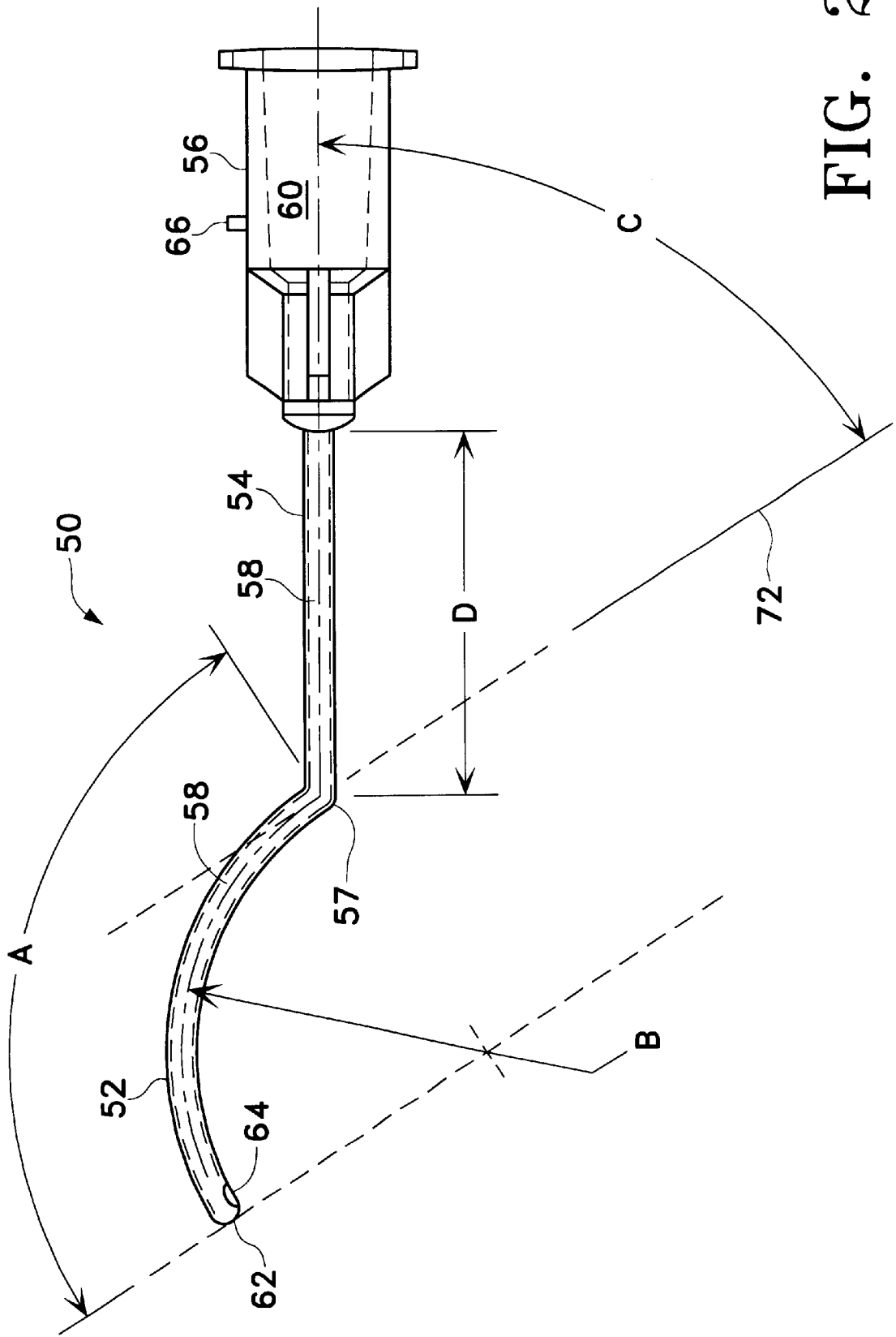
FIG. 2 is a side, partially sectional view schematically illustrating a cannula for creating the drug depot of FIG. 1 according to a preferred embodiment of the present invention.

Referring now to FIG. 2, a cannula 50 for creating drug depot 38 according to a preferred embodiment of the present invention is schematically illustrated. Cannula 50 generally includes a distal portion 52, a proximal portion 54, and a hub 56. A bend 57 separates distal portion 52 and proximal portion 54. A hollow bore 58 runs axially within distal portion 52 and proximal portion 54 and is fluidly coupled with a hollow bore 60 within hub 56.

Distal portion 52 preferably has a blunt tip 62 to prevent damage to blood vessels in the periocular tissues and to pass smoothly over sclera 16. An orifice 64 is located proximate tip 62 for delivery of a drug formulation. Orifice 64 is preferably located about 1 mm from tip 62 on the lower or interior side of distal portion 52 to minimize the possibility of connective tissue blockage. Orifice 64 may alternatively be located on the end, on the upper or exterior side, or on other portions of distal portion 52. In addition, distal portion 52 may have multiple orifices, if desired. Orifice 64 is preferably circular and preferably has a 0.025 inch diameter that insures a smooth, controlled delivery of drug. Alternatively, other shapes and sizes of orifice 64 may be used.

Distal portion 52 and proximal portion 54 are preferably formed out of 19 gauge needle stock. However, other sizes of tubing may be utilized depending on the viscosity and/or volume of material to be injected. Distal portion 52 and proximal portion 54 are preferably made of surgical stainless steel. Other conventional materials such as Teflon, other metals, metal alloys, polyethylene, polypropylene, other conventional plastics, or combinations of the foregoing may also be used. For example, distal portion 52 may be made from a plastic. As another example, a part of distal portion 52 proximate tip 62 may be made from plastic, and the remainder of distal portion 52 and proximal portion 54 may be made from metal. The plastic preferably has sufficient softness and/or flexibility to minimize the possibility of penetration of sclera 16 or Tenon's capsule 34 when cannula 50 is inserted into eye 10, as described hereinbelow. In addition, the length of the plastic portion of distal portion 52, as well as the specific plastic, are preferably selected so that distal portion 52 maintains its radius of curvature B when cannula 50 is inserted into eye 10.

Hub 56 is for removably coupling to a conventional syringe (not shown). Hub 56 preferably complies with Luer Taper Specification 70.1 of the American Standards Association. Hub 56 preferably includes a locator protuberance 66 that is coplanar with distal portion 52 and proximal portion 54. Protuberance 66 allows a physician to know the orientation of distal portion 52 even when it is inserted below Tenon's capsule 34. Hub 56 is preferably made of conventional plastics.

Referring to both FIGS. 1 and 2, distal portion 52 preferably has an arc length A and a radius of curvature B substantially equal to a radius of curvature of sclera 16 of an adult human eye 10 from insertion points 70a or 70b, each of which is about 5 mm to about 10 mm posterior of limbus 32. Arc length A and radius of curvature B insure that drug depot 38, and more specifically, a specific quantity of pharmaceutically active agent, is deposited on the outer surface of sclera 16 generally above macula 30.

Arc length A and bend 57 also limit the depth of insertion of cannula 50 along sclera 16, preventing tip 62 from accidentally contacting and damaging posterior ciliary arteries 40 or optic nerve 22. For an adult human eye 10 and for superior temporal or inferior temporal sub-Tenon insertion of cannula 50, arc length A is preferably about 15 mm to about 18 mm. Arc length A may be varied for patient's with smaller or larger than average adult eyes, for pediatric patient's with smaller eyes, or for different insertion points into Tenon's capsule 34. A tangent 72 of distal portion 52 at bend 57 is preferably formed at an angle C with respect to proximal portion 54. In addition to making bend 57 a physical limit to the insertion of cannula 50, angle C also raises the angle of hub 56 so that the face, bridge of the nose, and eyebrows of a patient to not interfere with the attached syringe. Angle C is also important to the successful delivery of drugs in the form of suspensions, emulsions, ointments, or gels, or drugs in such forms including bioerodable polymers or nonbioerodable polymers. Angle C is preferably no more than about 56 degrees. Angle C is most preferably about 56 degrees. Proximal portion 54 preferably has a length D of about 15 mm. Other angles and lengths may be used for angle C and length D for specific applications of cannula 50.

Radius of curvature B insures that distal portion 52 does not drag or put pressure on sclera 16 as cannula 50 is advanced to the proper position, minimizing the risk of sceral penetration. In addition, radius of curvature B eliminates the "tenting" or pulling away of Tenon's capsule 34 from sclera 16, minimizing the risk of penetration into the periocular tissues. For an adult human eye 10 and for superior temporal or inferior temporal sub-Tenon insertion of cannula 50, radius of curvature B is preferably about 11.5 mm to about 14 mm, and most preferably about 12.5 mm. Radius of curvature B may be varied for patients with smaller or larger than average adult eyes, for pediatric patients with smaller eyes, or for different insertion points into Tenon's capsule 34.

Cannula 50 may be used to inject a wide variety of drug formulations using the following preferred techniques. In a first preferred technique, a physician first anesthetizes eye 10 using conventional topical anesthetic drops. The patient is then instructed to look down and toward his or her nose. Next, the physician uses a 25 gage, ⅝ inch needle to penetrate both conjunctiva 36 and Tenon's capsule 34 at a point about 4 mm posterior to limbus 32 in the superior temporal quadrant of eye 10. The needle is then advanced along the outer surface of sclera 16 to a point about 8 mm to about 9 mm posterior of limbus 32. The physician then makes a small bleb of anesthesia, preferably about 1 mm to about 2 mm long, at this point. The physician then grasps the tissue raised by the bleb with a forceps, and then punctures a hole through conjunctiva 36 and Tenon's capsule 34 using an introducer needle. The introducer needle preferably has an outer diameter with the same gage as cannula 50 or one gage larger than cannula 50. Next, the physician draws a drug formulation into a conventional syringe using a conventional straight needle. The needle is removed and cannula 50 is attached to the syringe. All air is removed from the syringe and cannula 50 so that the drug formulation is at tip 62. The physician then introduces cannula 50 through the hole made by the introducer needle, with orifice 64 facing sclera 16. With distal portion 52 in close contact with the outer surface of sclera 16, cannula 50 is advanced toward the back of the eye until bend 57 is at the site of the hole made by the introducer needle. At this point, tip 62 is preferably located about 5 mm to about 6 mm from the center of optic nerve 22, and about 2 mm to about 3 mm from macula 30 so that the tip 62 is disposed proximate the macula 30. The physician then injects the drug formulation by actuating the syringe plunger, creating drug depot 38 on the outer surface of sclera 16 generally above macula 30. Alternatively, the above-described technique may be performed in the inferior temporal quadrant of eye 10, in which case the patient is instructed to look up and toward his or her nose.

In a second preferred technique, a physician first anesthetizes eye 10 using conventional topical anesthetic drops. Next, the patient is instructed to look down and toward his or her nose. Next, the physician creates a small incision in conjuctiva 36 and Tenon's capsule 34 at a point about 8 mm to about 9 mm posterior to limbus 32 in the superior temporal quadrant of eye 10 using fine scissors. The physician then draws a drug formulation into a conventional syringe, and then attaches cannula 50 to the syringe, as described above. Cannula 50 is then inserted through the incision with orifice 64 facing sclera 16. With distal portion 52 in close contact with the outer surface of sclera 16, cannula 50 is advanced toward the back of the eye until bend 57 is at the site of the incision. At this point, tip 62 is preferably located about 5 mm to about 6 mm from the center of optic nerve 22, and about 2 mm to about 3 mm from macula 30. The physician then injects the drug formulation by actuating the syringe plunger, creating drug depot 38 on the outer surface of sclera 16 generally above macula 30. If necessary, the incision may be sealed around cannula 50 using a purse suture to prevent reflux of the injected drug formulation. Alternatively, the above-described technique may be performed in the inferior temporal quadrant of eye 10, in which case the patient is instructed to look up and toward his or her nose.

Depending on the physicochemical properties of the drug formulation, drug depot 38 preferably provides controlled release of a pharmaceutically active agent to macula 30 and retina 20 via sclera 16 and choroid 18 for a period of weeks or months. As the use of cannula 50 causes no "tenting" or substantial stretching of Tenon's capsule 34, cannula 50 should result in significantly less trauma to eye 10 than conventional cannulae when repeated injections are required.

Cannula 50 can be used to deliver a wide variety of drug formulations to treat a wide variety of diseases of posterior segment 26. The drug formulation used to form drug depot 38 may be a solution, a suspension, an emulsion, an ointment, a gel forming solution, a gel, a bioerodable polymer, or a non-bioerodable polymer. The drug formulation used to form drug depot 38 may include one or more ophthalmically acceptable pharmaceutically active agents, and may also include conventional non-active incipients. Examples of pharmaceutically active agents suitable for this drug formulation are anti-infectives, including, without limitation, antibiotics, antivirals, and antifungals; antiallergenic agents and mast cell stabilizers; steroidal and nonsteroidal anti-inflammatory agents (such as nepafenac); cyclooxygenase inhibitors, including, without limitation, Cox I and Cox II inhibitors; combinations of anti-infective and anti-inflammatory agents; decongestants; anti-glaucoma agents, including, without limitation, adrenergics, β-adrenergic blocking agents, a-adrenergic agonists, parasypathomimetic agents, cholinesterase inhibitors, carbonic anhydrase inhibitors, and prostaglandins; combinations of anti-glaucoma agents; antioxidants; nutritional supplements; drugs for the treatment of cystoid macular edema including, without limitation, non-steroidal anti-inflammatory agents; drugs for the treatment of ARMD, including, without limitation, angiogenesis inhibitors and nutritional supplements; drugs for the treatment of herpetic infections and CMV ocular infections; drugs for the treatment of proliferative vitreoretinopathy including, without limitation, antimetabolites and fibrinolytics; wound modulating agents, including, without limitation, growth factors; antimetabolites; neuroprotective drugs, including, without limitation, eliprodil; and angiostatic steroids for the treatment of diseases or conditions of posterior segment 26, including, without limitation, ARMD, CNV, retinopathies, retinitis, uveitis, macular edema, and glaucoma. Such angiostatic steroids are more fully disclosed in U.S. Pat. Nos. 5,679,666 and 5,770,592. Preferred ones of such angiostatic steroids include 4,9(11)-Pregnadien-17α,21-diol-3,20-dione and 4,9 (11)-Pregnadien-17α,21-diol-3,20-dione-21-acetate. These preferred angiostatic steroids are preferably formulated as a suspension. A preferred non-steroidal anti-inflammatory for the treatment of cystoid macular edema is nepafenac. The conventional non-active excipients may include, but are not limited to, ingredients to enhance the stability, solubility, penetrability, or other properties of the pharmaceutically active agent or drug depot 38.

FIGS. 3A through 3E show additional preferred embodiments of cannulae for the creation of drug depot 38. Each of these cannulae have a proximal portion 54, hub 56, bend 57, and hollow bore 58 substantially identical to that described above for cannula 50 of FIG. 2. However, each of these cannulae has a unique distal portion. Hub 56 of each of these cannulae is removably coupled to a conventional syringe 80. Each of these cannulae can be used to create drug depot 38 directly on the outer surface of sclera 16 generally above macula 30 in a manner substantially similar to the techniques described above for cannula 50.

Figure 3A:
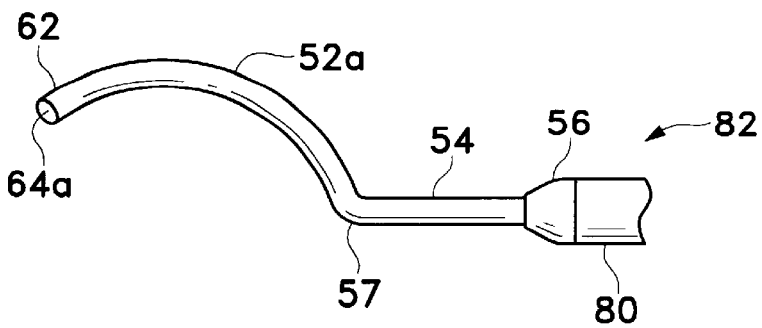
FIGS. 3A through 3E are side views schematically illustrating additional preferred embodiments of the cannula of FIG. 2.
Figure 3B:
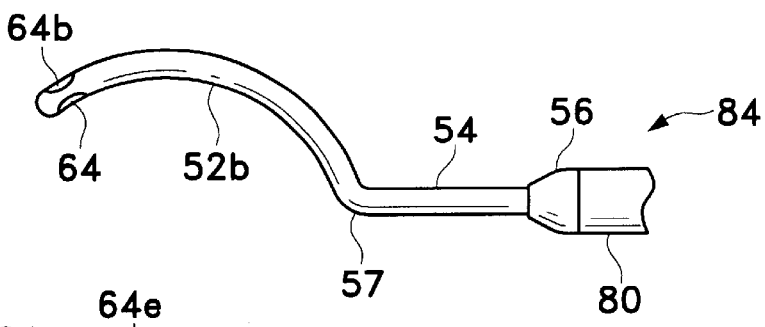

Cannula 82 of FIG. 3A has a distal portion 52a with a geometry substantially identical to distal portion 52 of cannula 50, except that an orifice 64a is located on the end of tip 62 of distal portion 52a. Similarly, cannula 84 of FIG. 3B has a distal portion 52b with a geometry substantially identical to distal portion 52 of cannula 50, except that tip 62 has two orifices, 64 and 64b. Orifice 64b is located on the upper or exterior side of distal portion 52b. Alternatively, although not shown in FIG. 3B, orifices 64 and 64b may be located laterally, on opposite sides of distal portion 52b.

Figure 3C:
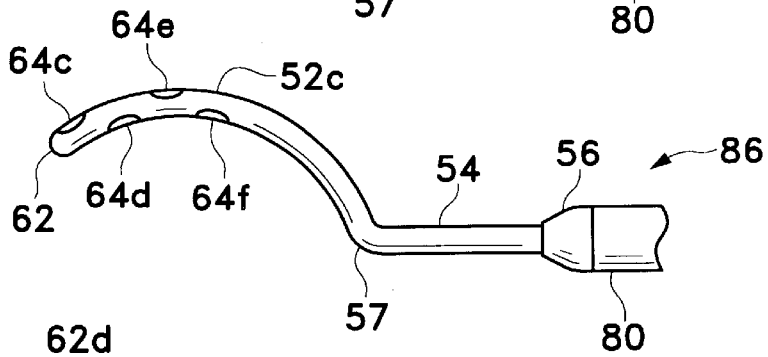

Cannula 86 of FIG. 3C has a distal portion 52c with a geometry substantially identical to distal portion 52 of cannula 50, except that a plurality of orifices 64c, 64d, 64e, and 64f are disposed on distal portion 52c proximate tip 62. Orifices 64c through 64f are preferably disposed on distal portion 52c in the alternating pattern shown in FIG. 3C. Cannula 86 is useful when it is desirable to create a larger drug depot 38. Distal portion 52c may be formed with more or less than the four orifices shown in FIG. 3C, or with a different pattern of orifices than shown in FIG. 3C, if desired.

Figure 3D:
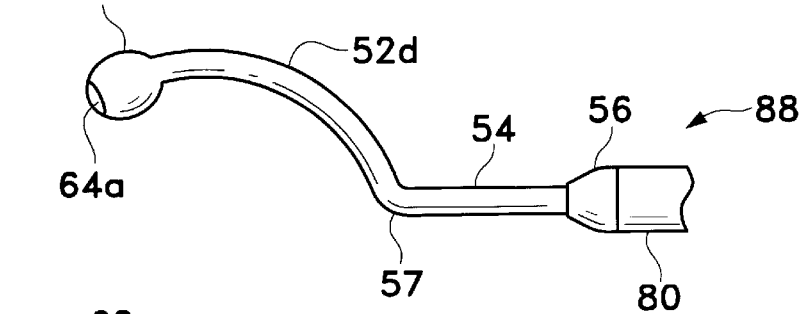

Cannula 88 of FIG. 3D has a distal portion 52d with a geometry substantially identical to distal portion 52a of cannula 82 of FIG. 3A, except that tip 62d has a globular or olive shape. Tip 62 thus serves as a scieral depressor, allowing a physician to view tip 62d through an ophthalmoscope as he or she guides cannula 88 along the outer surface of sclera 16. Tip 62 is preferably sized to create as small a pathway as possible between Tenon's capsule 34 and sclera 16, but still function as a scleral depressor. A small pathway minimizes the possibility of drug formulation flowing anteriorly from drug depot 38.

Figure 3E:
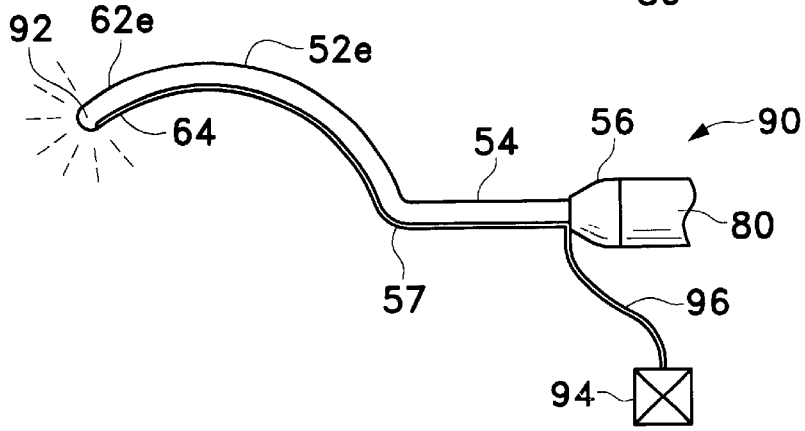

Cannula 90 of FIG. 3E has a distal portion 52e with a geometry substantially identical to distal portion 52 of cannula 50 of FIG. 2, except that tip 62e is also equipped with a fiber optic light source 92, allowing a physician to view tip 62e through an ophthalmoscope as he or she guides cannula 90 along the outer surface of sclera 16. A conventional power source 94 is electrically coupled to fiber optic light source 92 via conventional electrical wiring 96 that is preferably at least partially disposed within the wall of distal portion 52e and proximal portion 54. Fiber optic light source 92, power source 94, and wiring 96 may be incorporated into any of the cannulae disclosed in this application, if desired.

Figure 4:
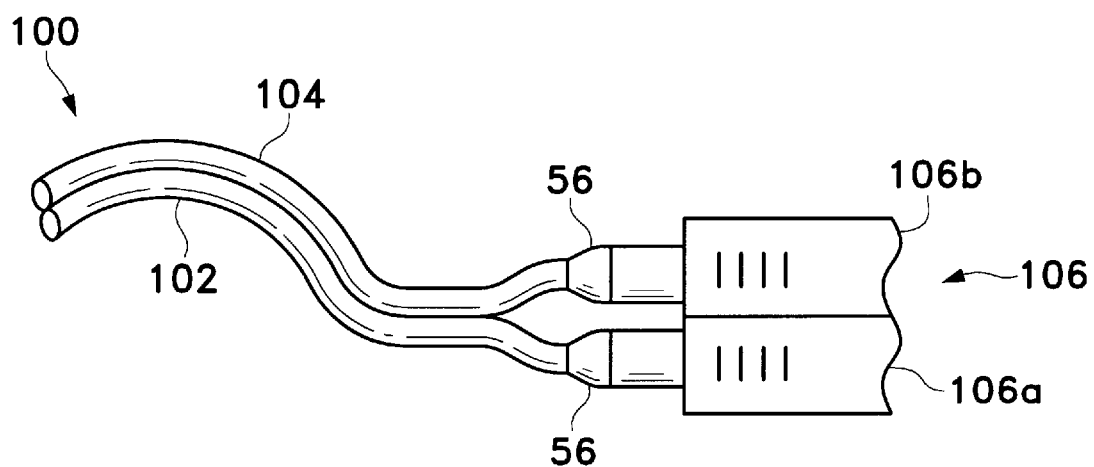
FIG. 4 is a side view schematically illustrating a preferred embodiment of the cannula of FIG. 2 having dual lumens.

FIG. 4 schematically illustrates a preferred embodiment of a cannula 100 for the creation of drug depot 38. Cannula 100 includes a lumen 102 having a geometry substantially identical to cannula 82 of FIG. 3A. Cannula 100 also includes a second, separate lumen 104 disposed adjacent to lumen 102 and having a geometry substantially identical to cannula 82 of FIG. 3A. Lumen 102 and lumen 104 are not in communication with each other as clearly shown in FIG. 4. Lumen 102 has a hub 56 removably coupled to a lumen 106a of a dual lumen syringe 106. Lumen 104 has a hub 56 removably coupled to a lumen 106b of dual lumen syringe 106.

Cannula 100 can be used to create drug depot 38 directly on the outer surface of sclera 16 generally above macula 30 in a manner substantially similar to the techniques described above for cannula 50. However, cannula 100 allows the delivery of two separate drug formulations while creating drug depot 38. Alternatively, lumen 104 of cannula 100 can be used to aspirate a non-bioerodable drug depot 38 that has dispensed all of its pharmaceutically active agent, and lumen 102 of cannula 100 can be used to inject a new drug depot 38.

Figure 5:
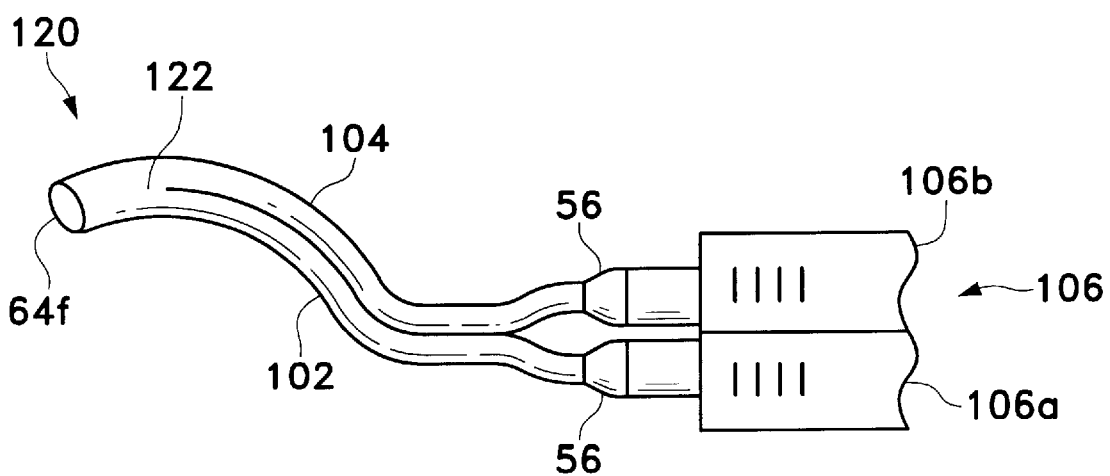
FIG. 5 is a side view schematically illustrating a second preferred embodiment of the cannula of FIG. 2 having dual lumens.
Figure 6:
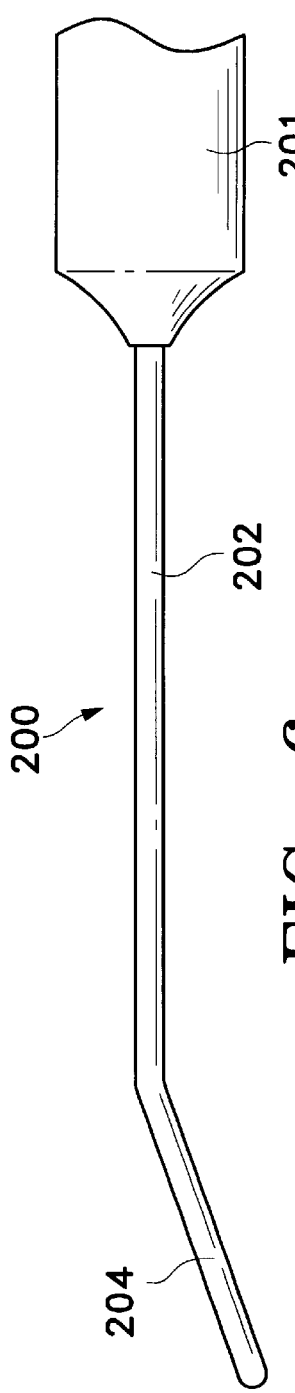
FIG. 6 is a side view schematically illustrating a first conventional cannula of the prior art.
Figure 7:
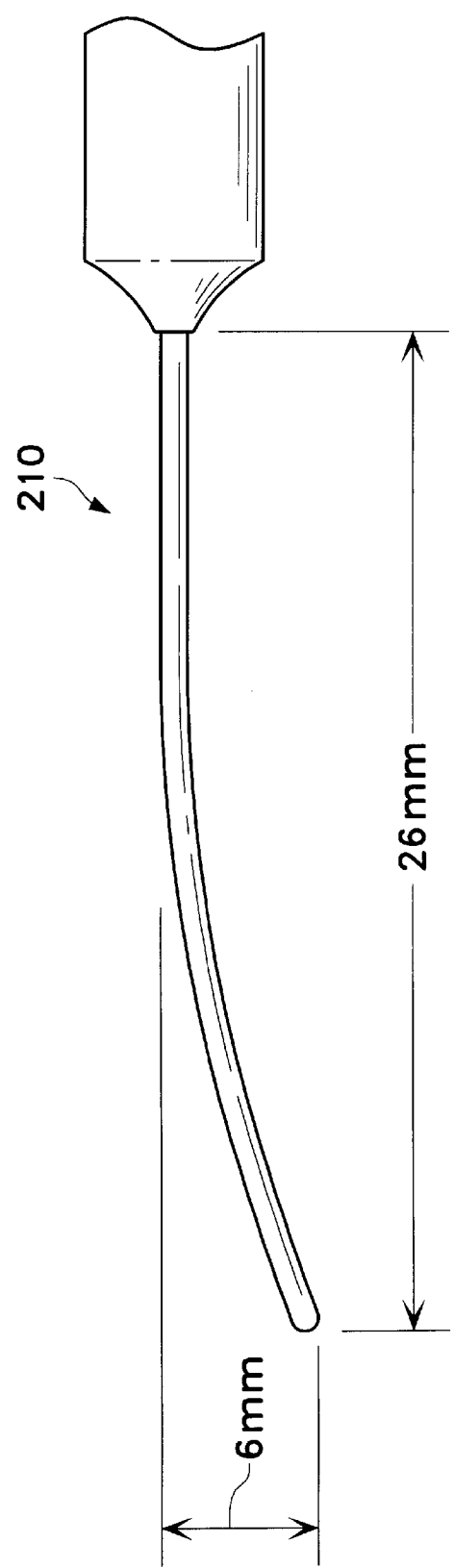
FIG. 7 is a side view schematically illustrating a second conventional cannula of the prior art.

FIG. 5 schematically illustrates a preferred embodiment of a cannula 120 for the creation of drug depot 38. Cannula 120 has a geometry substantially identical to that of cannula 100, except that lumen 102 and lumen 104 join at a point 122 proximate a single orifice 64ƒ near the distal portions of the cannula such that lumen 102 and lumen 104 are in communication with each other at the point 122 as closely shown in FIG. 5.

Cannula 120 can be used to create drug depot 38 directly on the outer surface of sclera 16 generally above macula 30 in a manner substantially similar to the techniques described above for cannula 50. However, cannula 120 allows the delivery of two separate formulations that require mixing just prior to injection out of orifice 64ƒ.

From the above, it may be appreciated that the present invention provides improved apparatus and methods for sub-Tenon delivery of a drug depot to the posterior segment of a human eye proximate the macula, The apparatus and methods of the present invention increase patient safety, are easy for the physician to use, are capable of delivering a wide spectrum of formulations, and are capable of being performed in an outpatient setting. The apparatus and methods of the present invention are especially useful for localized delivery of pharmaceutically active agents to the posterior segment of the eye to combat ARMD, CNV, retinopathies, retinitis, uveitis, macular edema, glaucoma, and other posterior segment diseases. The apparatus and methods of the present invention are also particularly useful for the sub-Tenon delivery of drugs in the form of suspensions, emulsions, ointments, or gels, or drugs in such forms including bioerodable polymers or non-bioerodable polymers.

The present invention is illustrated herein by example, and various modifications may be made by a person of ordinary skill in the art. For example, although the carnulae of the present invention have been described above in connection with the preferred sub-Tenon drug delivery generally above the macula, the cannulae can be used to deliver drugs directly on the outer surface of the sclera, below the Tenon's capsule, and generally above portions of the retina other than the macula. As another example, the arc length and/or radius of curvature of the distal portions of the cannulae may be modified to deliver drugs within the Tenon's capsule or the sclera, generally above the macula or other portions of the retina, if desired.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A cannula, comprising:
   a distal portion having a radius of curvature substantially equal to a radius of curvature of a globe of a human eye;
   a proximal portion; and
   a bend separating said distal portion and said proximal portion,
   wherein a tangent of said distal portion at said bend is disposed at an angle of no more than about 56 degrees with respect to said proximal portion.

2. The cannula of claim 1 wherein said distal portion comprises an arc length of about 15 mm to about 18 mm.

3. The cannula of claim 1 further comprising:
   a hub coupled to said proximal portion for removably coupling to a syringe; and
   a hollow bore disposed axially within said distal portion and said proximal portion.

4. The cannula of claim 3 wherein said distal portion has a plurality of orifices, each of said orifices communicating with said hollow bore.

5. The cannula of claim 3 wherein said bend is adopted to prevent said syringe from interfering with a patient's face, bridge of the nose, and eyebrows when said distal portion is inserted into said eye.

6. The cannula of claim 1 wherein said distal portion comprises an interior side and a tip having an orifice on said interior side.

7. The cannula of claim 1 wherein said distal portion has a radius of curvature substantially equal to a radius of curvature of a sclera of said eye.

8. The cannula of claim 1 wherein said radius of curvature of said distal portion is about 11.5 mm to about 14 mm.

9. The cannula of claim 1 wherein said distal portion is made of plastic.

10. The cannula of claim 1 wherein said distal portion comprises a tip and an orifice proximate said tip, and wherein a part of said distal portion proximate said tip is made of plastic, and a remainder of said distal portion is made from metal.

11. The cannula of claim 1 wherein said angle is about 56 degrees.

12. The cannula of claim 1 wherein said distal portion comprises a tip having an olive shape.

13. The cannula of claim 1 wherein said distal portion comprises:
    a tip; and
    a fiber optic light source disposed at said tip.

14. The cannula of claim 1 wherein said distal portion, said proximal portion, and said bend comprise a first lumen, and further comprising:
    a second lumen having a geometry substantially similar to said first lumen and disposed adjacent said first lumen.

15. The cannula of claim 14 wherein said first lumen and second lumen are not in communication.

16. The cannula of claim 14 further comprising a tip, and wherein said first lumen and said second lumen are in communication proximate said tip.

17. The cannula of claim 1 wherein said distal portion and said proximal portion are formed of 19 gauge needle stock.

18. A method of delivering a drug to a human eye, comprising the steps of:
    inserting a cannula below a Tenon's capsule and above a sclera of said human eye at a point posterior to a limbus of said eye, said cannula comprising:
        a distal portion having a radius of curvature substantially equal to a radius of curvature of a globe of said human eye;
        a proximal portion; and
        a bend separating said distal portion and said proximal portion,
        wherein a tangent of said distal portion at said bend is disposed at an angle of no more than about 56 degrees with respect to said proximal portion;
    injecting a drug formulation through said cannula to form a drug depot on an outer surface of said sclera.

19. The method of claim 18 wherein said distal portion of said cannula comprises a tip, and further comprising the step of disposing said tip proximate a macula of said eye.

20. The method of claim 18 wherein said drug formulation comprises a suspension.

21. The method of claim 20 wherein said suspension comp rises a bioerodable polymer.

22. The method of claim 20 wherein said suspension comprises a non-bioerodable polymer.

23. The method of claim 18 wherein said drug formulation comprises an emulsion.

24. The method of claim 18 wherein said drug formulation comprises an ointment.

25. The method of claim 18 wherein said drug formulation forming solution comprises a gel.

26. The method of claim 18 wherein said distal portion has a radius of curvature substantially equal to a radius of curvature of a sclera of said eye.

27. The method of claim 18 wherein said inserting step comprises inserting said cannula into a superior temporal quadrant of said eye.

28. The method of claim 18 wherein said inserting step comprises inserting said cannula into an inferior temporal quadrant of said eye.

29. The method of claim 18 wherein said drug formulation comprises a pharmaceutically active agent selected from the group consisting of 4,9(11)-Pregnadien-17α,21-diol-3,20-dione and 4,9(11)-Pregnadien-17α,21-diol-3,20-dione-21-acetate.

30. The method of claim 18 wherein said drug formulation comprises eliprodil.

31. The method of claim 18 wherein said drug formulation comprises nepafenac.

32. A method of delivering a drug to a human eye, comprising the steps of:

inserting a cannula below a Tenon's capsule and above a sclera of said human eye at a point posterior to a limbus of said eye, said cannula having a distal portion having a radius of curvature substantially equal to a radius of curvature of a globe of said eye; and injecting a drug formulation through said cannula to form a drug depot on an outer surface of said sclera, said drug formulation comprising a pharmaceutically active agent selected from the group consisting of 4,9(11)-Pregnadien-17α,21-diol-3,20-dione and 4,9(11)-Pregnadien-17α,21-diol-3,20-dione-21-acetate.

33. The method of claim 32 wherein said injecting step comprises forming said drug depot on said outer surface of said sclera generally above a macula of said eye.

34. The method of claim 32 further comprising disposing a tip of said distal portion proximate said macula of said eye.

35. A cannula, comprising:

a hub for removably coupling to a syringe;

a proximal portion; and a distal portion having a tip, an orifice proximate said tip, and a radius of curvature substantially equal to a radius of curvature of a globe of a human eye, wherein a part of said distal portion proximate said tip is made of plastic.

36. The cannula of claim 35 wherein a remainder of said distal portion is formed of metal.

* * * * *

UNITED STATES PATENT AND TRADEMARK OFFICE
CERTIFICATE OF CORRECTION

PATENT NO.    : 6,413,245 B1
DATED         : July 2, 2002
INVENTOR(S)   : Yaacobi, Yoseph; Clark, Abbot; Dahlin, David; Struble, Carig; Marsh, David and York, Billie It is certified that error appears in the above-identified patent and that said Letters Patent is hereby corrected as shown below:

Column 10,
Line 4, delete "adopted" and insert -- adapted -- in its place.

Column 11,
Line 6, delete "forming solution comprises a gel" and insert -- comprises a gel forming solution -- in its place.

Column 12,
Line 15, delete the second "said" and insert -- a -- in its place.

Signed and Sealed this

Twenty-ninth Day of October, 2002

*Attest:*

JAMES E. ROGAN
*Director of the United States Patent and Trademark Office*

*Attesting Officer*